United States Patent [19]

Eftekhar

[11] 4,404,692
[45] Sep. 20, 1983

[54] CENTERING SYSTEM FOR HIP REPLACEMENT

[76] Inventor: Nas S. Eftekhar, 25 Paddock Rd., Hohokus, N.J. 07423

[21] Appl. No.: 301,579

[22] Filed: Sep. 14, 1981

[51] Int. Cl.³ .............................................. A61F 1/04
[52] U.S. Cl. ...................................... 3/1.912; 3/1.91; 128/92 C
[58] Field of Search ........... 128/92 E, 92 EB, 92 EC, 128/92 BC, 92 C, 92 CA; 3/1, 1.9, 1.91, 1.911, 1.912, 1.913

[56] References Cited

U.S. PATENT DOCUMENTS

| | | | |
|---|---|---|---|
| 3,782,373 | 1/1974 | Smythe | 3/1.913 X |
| 3,814,089 | 6/1974 | Deyerle | 3/1.913 X |
| 3,815,590 | 6/1974 | Deyerle | 3/1.913 X |
| 3,857,389 | 12/1974 | Amstutz | 3/1 X |
| 4,080,666 | 3/1978 | Fixel | 3/1.913 X |
| 4,268,920 | 5/1981 | Engelbrecht et al. | 3/1.911 |
| 4,275,717 | 6/1981 | Bolesky | 128/92 BA |
| 4,276,659 | 7/1981 | Hardinge | 3/1.9 |
| 4,293,962 | 10/1981 | Fuson | 3/1.9 |

FOREIGN PATENT DOCUMENTS 517193  7/1979  U.S.S.R. ........................ 128/92 C

Primary Examiner—Richard J. Apley
Assistant Examiner—David J. Isabella
Attorney, Agent, or Firm—Sherman & Shalloway

[57] ABSTRACT

The present invention provides a system for centering proximally and distally a hip replacement. The system comprises a trial hip prosthesis for centering proximally the hip replacement and a device adapted for insertion into the medullary canal for centering distally the hip replacement, the device being provided with means to receive and center the stem in the hip replacement. A method for obtaining a proximally and distally centered total replacement is also provided.

18 Claims, 18 Drawing Figures

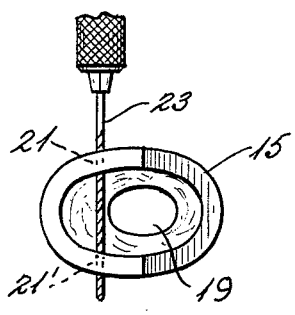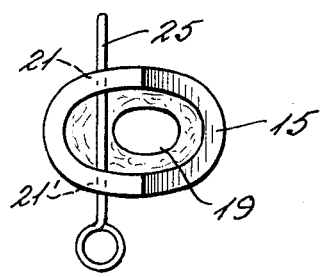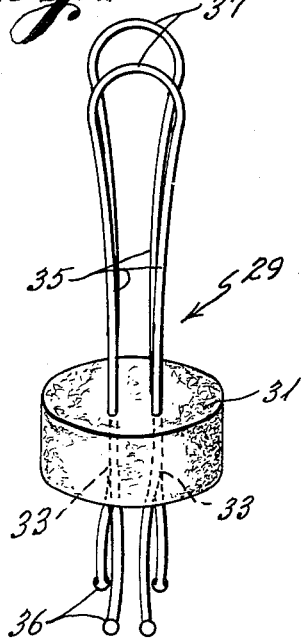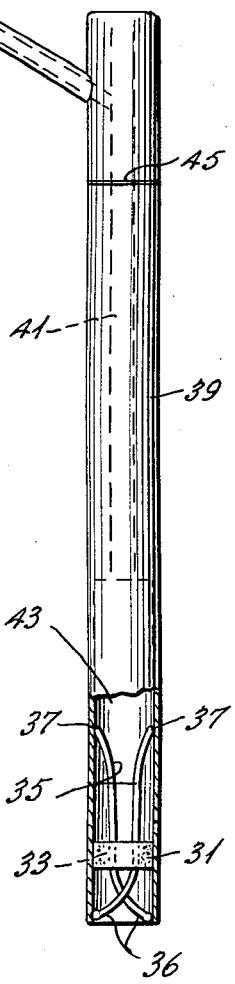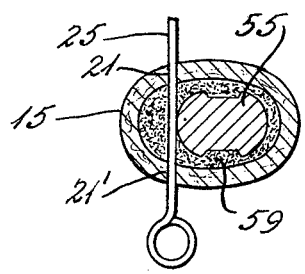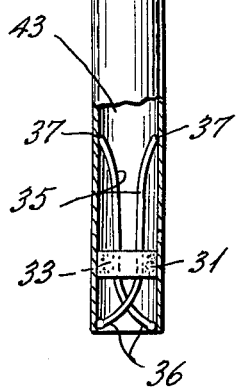

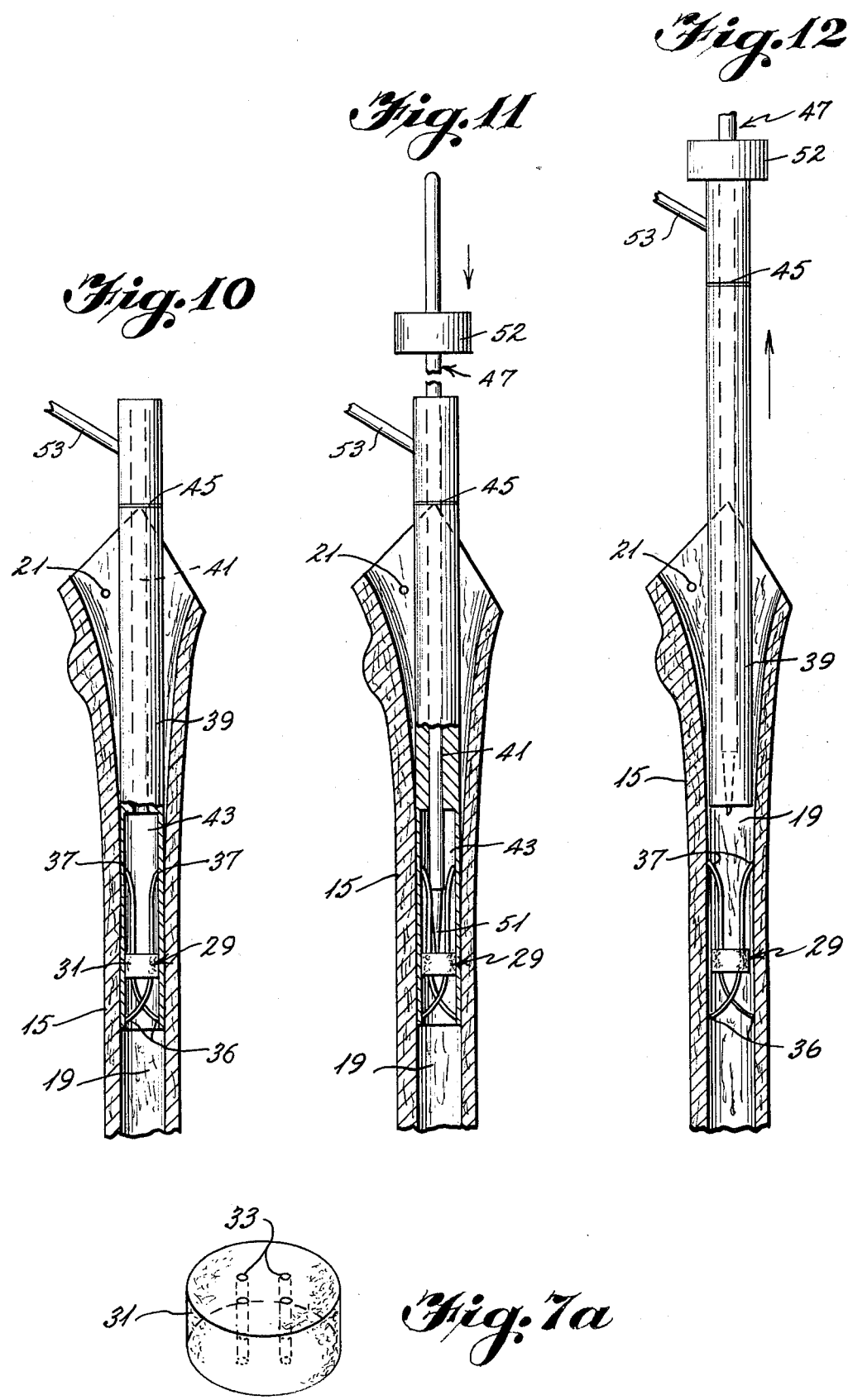

CENTERING SYSTEM FOR HIP REPLACEMENT

BACKGROUND OF THE INVENTION

1. Field of the Invention

This invention is related to hip replacement. More particularly, this invention is related to a distally and proximally centered hip replacement.

2. Description of the Prior Art

The replacement of both of the femoral head and the acetabulum by prosthesis cemented into the bone as surgical treatment of a fractured hip or chronic arthritis of the hip is well known. In general, the conventional technique comprises removing the head and a part of the neck of the femur. The soft cancellous bone that lies within the remains of the neck and shaft of the femur is removed to facilitate the introduction of the bone cement and the hip prosthesis. If the acetabulum also needs repair, all remnants of articular cartilage are removed from the acetabulum. A cup which will accommodate the head or ball of the hip prosthesis is then cemented to the acetabulum by means of bone cement. Thereafter, the hip prosthesis is inserted into the femoral shaft. A trial reduction is then made. When it is apparent that reduction will just be possible, the hip prosthesis is removed and the upper part of the shaft of the femur is filled with bone cement. The hip prosthesis is then reinserted and allowed to set. As can be readily appreciated, the alignment or centering of the hip prosthesis within the shaft of the femur is of utmost importance if the artificial hip joint is to function properly.

SUMMARY OF THE INVENTION

The present invention provides a system for centering a hip prosthesis or replacement distally and proximally in the shaft of the femur. The system comprises a femoral trial prosthesis for determining the mediolateral position of the upper stem of the prosthesis in the shaft of the femur and a device for centering distally the stem of the prosthesis, the device comprising a cylindrical plug which is inserted in the medullary canal in the femur, the plug having a plurality of wires extending longitudinally therethrough to accommodate and center the stem of the prosthesis. The plug has the additional function of obliterating the medullary canal of the femur, thus producing pressure within the upper femur at the time of the insertion of the cement for improved cement injection.

The present invention also provides a method for centering proximally and distally a hip replacement in the femur.

In another aspect of the present invention, a femoral trial prosthesis for determining the medio-lateral position of the upper stem of a femoral prosthesis in the femur is provided.

In a further aspect of the present invention, a device for centering and accommodating the stem of a femoral prosthesis in the medullary canal in the femur of a patient is provided.

BRIEF DESCRIPTION OF THE DRAWINGS

FIG. 5 shows a top view of a hole being drilled to accommodate the centering pin for the femoral trial prosthesis of the present invention.

FIG. 6 shows a top view of the placement of the centering pin to mark the centered position of the femoral trial prosthesis of the present invention.

FIG. 7 illustrates the device for centering distally the stem of a hip replacement of the present invention.

FIG. 7a illustrates the cylindrical plug which forms a part of the centering device shown in FIG. 7.

FIG. 8 illustrates a delivery tube for the distally centering device of FIG. 7.

FIG. 9 shows a plunger used in connection with the delivery tube of FIG. 8.

FIGS. 10–12 illustrate the procedure used in inserting the distally centering device of the present invention.

FIG. 17 shows the cross-sectional view taken along line 17—17 in FIG. 15.

DETAILED DESCRIPTION OF THE PREFERRED EMBODIMENTS

According to the present invention, there is provided a system for centering, distally and proximally, a hip replacement in the shaft of a patient's femur. The system comprises a femoral trial prosthesis and a device for centering distally the stem of the hip replacement.

Figure 1:
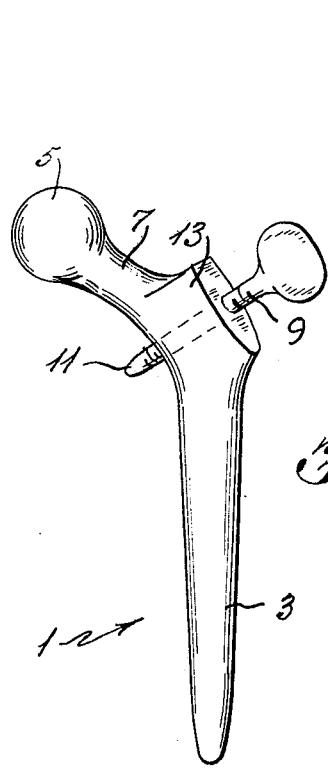
FIG. 1 illustrates the femoral trial prosthesis of the present invention.

With reference to the drawings, FIG. 1 shows the present femoral trial prosthesis for centering proximally a hip replacement. The trial prosthesis generally indicated at 1 comprises a stem 3 adapted to be fitted in the femur of a patient, a ball member 5 adapted to be fitted in the acetabulum or cup if the acetabulum is to be replaced, the ball member 5 and stem 3 being connected by neck portion 7. The stem 3, ball member 5 and neck portion 7 can be formed integrally. A laterally extending adjusting means is provided in the stem below the neck portion for centering proximally the femoral trial prosthesis with respect to the upper medullary canal of the femur. In FIG. 1, the adjusting means is in the form of a threaded screw 9 having one end 11 extending out of the prosthesis below neck portion 7 to contact the medullary canal. As shown in FIG. 1, the top portion of the trial prosthesis is formed into the shape of a wedge 13. Stem 3 may have any suitable length for use in hip replacements or prostheses. The angle with which neck portion 7 makes with stem 3 can be varied widely depending on design preference. Threaded screw 9 extends at an angle of from about 40 to about 60 degrees with respect to vertical stem 3. Hence, the present trial prosthesis has the general shape of the letter Y with the ball member 5 and adjustable means 9 forming the two upward projecting arms and stem 3, the vertical portion. As to the material which can be used in making the trial prosthesis, conventional materials generally utilized in making prostheses or trial prostheses can be used. The length of neck portion 7, stem 3 and the diameter of ball member, i.e., the overall dimensions of the trial prosthesis, are selected according to the size of the patient.

Figure 2:
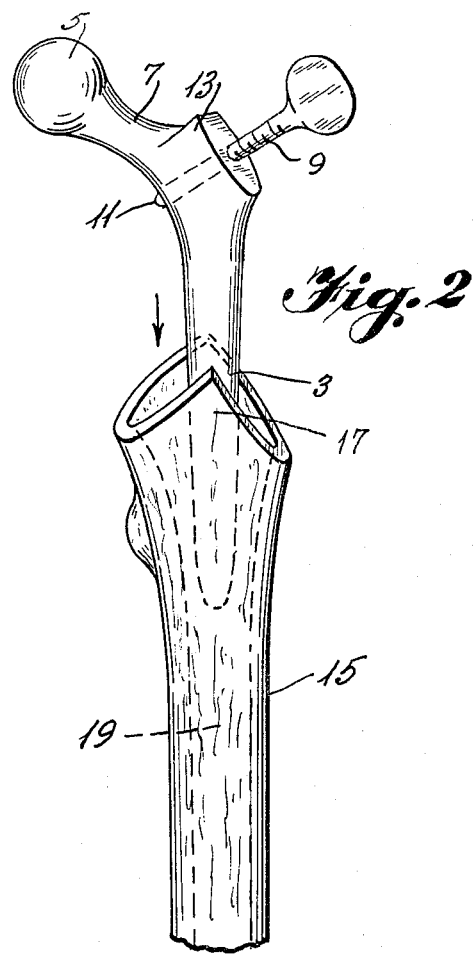
FIG. 2 shows the partial insertion of the femoral trial prosthesis into the shaft of a patient's femur.
Figure 3:
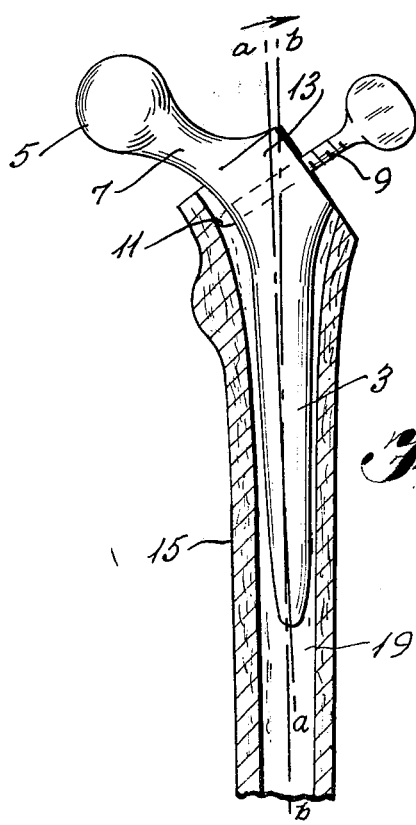
FIG. 3 shows a proximally non-centered femoral trial prosthesis.
Figure 4:
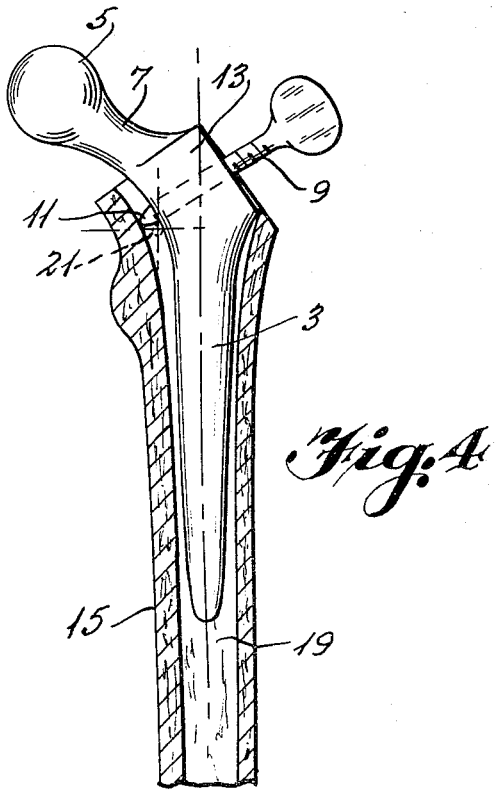
FIG. 4 illustrates a properly proximally centered femoral trial prosthesis.

FIGS. 2-4 illustrate the manner in which the femoral trial prosthesis is applied to the shaft of the patient's femur. As shown in FIG. 2, the head and preferably the greater trochanter of the femur 15 are removed so that the upper end 17 of the femur is in the form of a wedge, similar to upper end 13 of trial prosthesis 1. The soft cancellous bone that lies within the shaft of the femur is removed to expose the medullary canal 19. Thereafter, the femoral trial prosthesis 1 is inserted completely into the medullary canal 19, as shown in FIG. 3 which illustrates that the proximal end of trial prosthesis 1 is not properly centered. To center the prosthesis, screw 9 is turned either clockwise or counterclockwise to move prosthesis 1 closer to or further away from the upper medullary canal. In FIG. 3, the axis of prosthesis 1 is aligned with line 1—1 which is improper and should be moved to coincide with line b—b. Accordingly, screw 9 is turned until the proximal end is properly centered within the opening of the upper medullary canal, as shown in FIG. 4.

Thereafter, the hip is reduced (relocated) with femoral trial prosthesis 1 to ensure (a) a full range of motion, (b) appropriate tension without tendency to dislocate, and (c) a push-pull would allow no more than 5 mm of separation between components.

To mark the position of the femoral trial prosthesis, a centering pin is driven through the most proximal section of the femur. To accommodate the pin, two holes 21 and 21' in the front and back portions of the femur 15 are made by means of drill 23, as shown in FIG. 5. In drilling the holes, precaution is taken so as to avoid drilling through the trial prosthesis itself. Thereafter, the drill is removed and centering pin 25 is inserted, as illustrated in FIG. 6. With the insertion of pin 25, femoral trial prosthesis 1 is properly disposed in the opening in the upper medullary canal. Centering pin 25 can be of any convenient diameter and 3/32 inch has been found particularly suitable.

The device for centering distally the stem of a hip replacement is shown generally at 29 in FIG. 7. Device 29 comprises a cylindrical plug 31 having a plurality of openings 33 extending along the longitudinal axis thereof. Usually, four openings 33 are provided as illustrated in FIG. 7a. Preferably, plug 31 is made of a high density polyethylene and has a diameter which is less than the diameter of the medullary canal by from about 0.3 to 0.7 mm, preferably 0.5 mm, to allow for passage of air as pressure is built up proximally when bone cement is introduced thereinto. Extending through the openings 33 is a means for accommodating and centering the stem of the above-described femoral trial prosthesis or hip replacement implant. This means comprises a plurality of rods or wires which are bent into a generally U-shape. As shown in FIG. 7, two of these U-shaped wires 35 are used to form the centering means. Each of the arms of the U-shaped wire forming the open end thereof is fed through an opening 33 in plug 31. The diameters of the wires and the openings in the plug are about the same so that they permit easy insertion of the wires. The wires are formed of alloys which are conventionally used in the manufacture of prostheses. The closed end 37 of each of the U-shaped wires is bent, along the plane of the U-shaped wire, away from the stem of the hip replacement to be inserted so that the closed ends may retract or expand to accommodate and center the tip of the stem. In addition, the open end 36 of the U-shaped wire is bent along the plane of the wire so that the open end 36 contacts the interior surface of the medullary canal. As a result, both the open and closed ends 36, 37 can contact the interior surface of the medullary canal and exert pressure thereon to prevent the device 29 from undesirable movement.

The function of centering device 29 is twofold. Firstly, the device centers the tip of the stem of the hip prosthesis within the medullary canal. Secondly, cylindrical plug 31 clogs or plugs the medullary canal when bone cement is introduced to provide more complete filling of the canal and a better pressure injection within the interior architecture of the bone. In addition, the plug prevents the bone cement from extending too far distally in the canal, i.e., beyond the point where it is useful.

To insert centering device 29, the following procedure is used. A delivery tube of appropriate size is inserted into the medullary canal to determine the size of the canal at the level of the tip of the stem of the hip replacement. As detailed in FIG. 8, delivery tube 39 comprises a hollow cylindrical tube having two sections with different interior diameters 41 and 43. As is apparent, tube 39 can have only one interior diameter which is sufficiently large for storing centering device 29 therein. As shown in FIG. 8, the distal end of delivery tube 39 to be inserted into the medullary canal has an enlarged interior diameter which is of sufficient length to accommodate a distally centering device 29. Near the proximal end of the delivery tube 39 exterior markings 45 are provided which indicate the appropriate level to which the delivery tube should be inserted into the medullary canal. This level varies depending on the length of the stem to be inserted.

After ascertaining the size of the canal, an appropriately sized centering device 29 is inserted into section 43 of delivery tube 39. Thereafter, delivery tube 39 is inserted into the medullary canal 53 to the appropriate depth, as shown in FIG. 10.

The centering device 29 is pushed out of the delivery tube by plunger 47 the construction of which is shown in FIG. 9. Plunger 47 comprises a cylindrical shaft 49 having pointed tip 51 at one end. The other end of the shaft is provided with shoulder portion 52. The diameter of the shaft is smaller than that of section 41 in delivery tube 39. The length of shaft 49 is such that it exceeds the length of delivery tube 39 by about 1 to 3 mm. FIG. 11 illustrates the insertion of the entire length of plunger 47 into delivery tube 39 to push centering device 29 out of tube 39. When the open ends 36 of the U-shaped wires 35 are pushed out of delivery tube 39, they exert pressure against the interior of the medullary canal so that as the delivery tube and plunger are withdrawn, centering device 29 is lodged at a fixed location. Both the delivery tube and plunger are then withdrawn completely from the medullary canal, thus completing the placement of centering device 29 therein.

Figure 13:
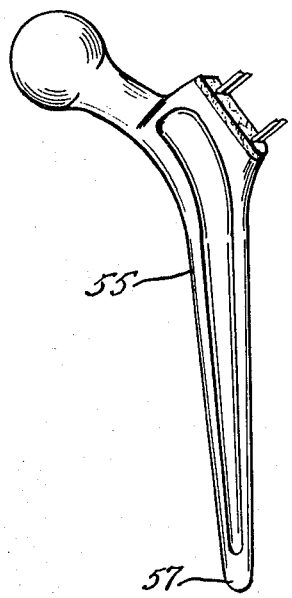
FIG. 13 shows a hip replacement useful in conjunction with the centering system of the present invention.
Figure 14:
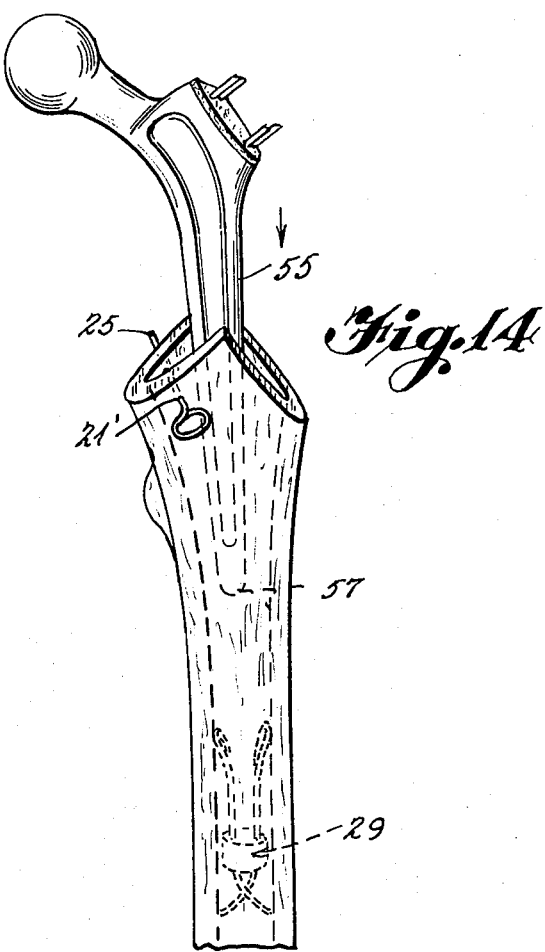
FIG. 14 illustrates the partial insertion of the hip implant after the centering pin and distally centering device have been placed in the femur.
Figure 15:
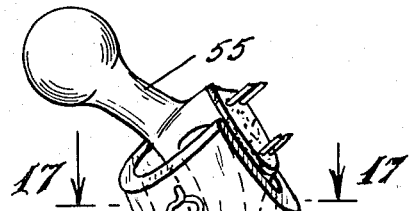
FIG. 15 illustrates the complete insertion of the hip replacement.
Figure 16:
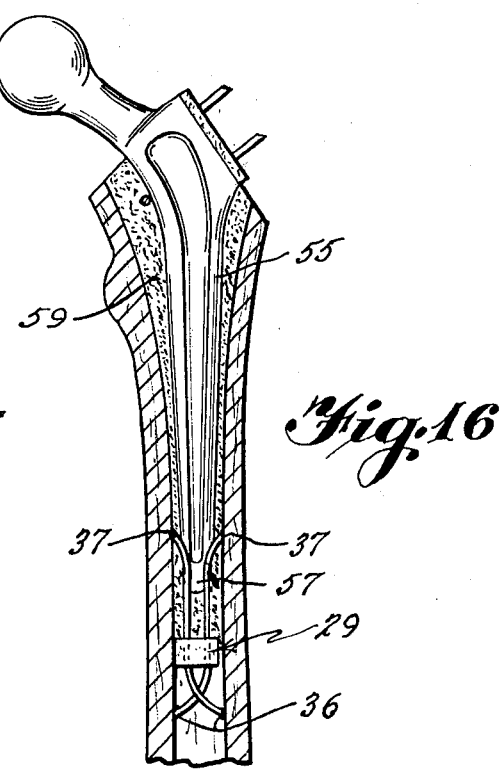
FIG. 16 shows a properly centered hip replacement.

To center proximally and distally a hip replacement, the system described herein can be used. First, the femoral trial prosthesis is placed into the upper medullary canal and centered proximally as described previously and illustrated in FIGS. 2 to 4. Centering pin is then inserted to ascertain the centered position, as shown in FIGS. 5 and 6. Thereafter, the trial prosthesis and, if necessary, the centering pin are removed. Device 29 for distally centering the stem of a hip replacement is then inserted into the medullary canal in the manner described previously and as hown in FIGS. 7 to 12. Centering pin 25, if removed, is then re-inserted across the femur. The medullary canal is then filled with a suitably bone cement. The hip replacement shown in FIG. 13 and having a configuration similar to femoral trial prosthesis 1 is inserted into the medullary canal, as shown in FIGS. 14, 15 and 17. The tip 57 of the stem of hip replacement 55 is inserted into the opening defined by the bent closed ends 37 of U-shaped wires 35 so that the stem is centered distally thereby. Centering pin 25 ascertains that the hip replacement is centered proximally within the upper medullary canal. After the cement has cured, centering pin 25 may be removed to provide a hip replacement which is properly centered proximally and distally in the shaft of the femur, as shown in FIG. 16.

In the procedure described above, it is disclosed that the trial prosthesis is first centered proximally and then distally. However, the distally centering device can be inserted first, with the trial prosthesis being centered proximally thereafter, depending on the preference of the surgeon conducting the surgical procedure.

Thus, there is provided a system, apparatus, and method for centering, both proximally and distally, a total hip replacement in the femur of a patient. It is further pointed out that the distally centering device described herein can be used to center the stem of any hip replacement or prosthesis, the configuration or construction of such hip replacement not necessarily being the same or similar to that disclosed herein. Furthermore, the proximal centering device described herein can be used to proximally center the stem of a hip prosthesis which does not necessarily have the same or similar configuration or structure as that disclosed herein, as long as the hip implant structure corresponds appropriately to the trial prosthesis configuration and utilizes the described proximal centering features. It is also understood that the centering devices of this invention can be used in conjunction with each other or individually to center distally or proximally the hip prosthesis, as required by the needs of the patient.

The present centering system is adapted for use in conjunction with a hip replacement system described in the present inventor's co-pending application entitled "Total Hip Replacement System" Ser. No. 301,577 filed Sept. 14, 1981, the disclosure of which is incorporated herein by reference.

What is claimed is:

1. A trial hip prosthesis for centering proximally a hip replacement in the upper medullary canal in the femur of a patient comprising:
   a stem adapted to be fitted in the femur of the patient,
   a ball member,
   a neck portion connecting said stem and said ball member, and
   a laterally extending adjusting means disposed in said stem below the neck portion and having one end extending laterally out of the prosthesis below the neck portion to contact and not penetrate the medullary canal to selectively adjust the distance between the trial hip prosthesis and the upper medullary canal so as to center proximally said prosthesis with respect to the upper medullary canal of the femur of said patient.

2. The prosthesis of claim 1 wherein said adjusting means comprises a threaded screw having one end extending out of the prosthesis below the neck portion to contact the medullary canal.

3. The prosthesis of claim 2 wherein the other end of said screw also extends out of the prosthesis.

4. A hip prosthesis system comprising the prosthesis of claim 3 and a pin for marking the centered position of said trial prosthesis, said pin adapted to be driven through the most proximal section of the femur to contact the lower surface of the upper portion of said stem.

5. A device for centering distally a hip replacement and plugging the medullary canal in the femur of a patient comprising
   a substantially cylindrical plug for coaxial insertion into and blockage of the medullary canal in the femur of the patient, said plug being provided with a plurality of through bores or openings so oriented to be parallel to the longitudinal axis of the plug, and
   means for accommodating and centering the distal end of the stem of the hip replacement, said means comprising a plurality of U-shaped wires each having an open end with two arms and a closed end, each arm of said U-shaped wires passing through one opening in said plug, the closed end of the U-shaped wire being directed toward the hip replacement, the closed ends of the wires being bent, along the plane formed by the arms of the U-shaped wire, away from the stem of the replacement to define an expansible and retractable guide to accommodate and center said distal end of the hip replacement, the open end of each of said U-shaped wire extending out of the openings in said plug being bent to contact and exert pressure on the medullary canal.

6. The device of claim 5 wherein said plug comprises four openings through which two U-shaped wires extend.

7. The device of claim 5 wherein said plug has a diameter from about 0.3 to 0.7 mm less than that of the medullary canal.

8. The device of claim 1 wherein said plug is made of high density polyethylene.

9. An apparatus for centering proximally and distally a hip replacement in the femur of a patient comprising
   (A) a trial hip prosthesis for centering proximally the hip replacement comprising
      (i) a stem adapted to be fitted in the femur of a patient,
      (ii) a ball member,
      (iii) a neck portion connecting said stem and said ball member, and
      (iv) a laterally extending adjusting means disposed in said stem below the neck portion and having one end extending laterally out of the prosthesis below the neck protion to contact and not penetrate the medullary canal to selectively adjust the distance between the trial hip prosthesis and the upper medullary canal so as to center said prosthesis with respect to the upper medullary canal of said femur,
   (B) a centering pin adapted to be inserted across said femur to mark the centered position of said trial hip prosthesis, and
   (C) a device for centering distally said hip replacement comprising
      (i) a cylindrical plug for coaxial insertion into and blockage of the medullary canal in said femur, said plug being provided with a plurality of through bores or openings so oriented to be parallel to the longitudinal axis of the plug, and (ii) means for accommodating and centering distally the distal end of the stem of said hip replacement, said means comprising a plurality of U-shaped wires each having an open end with two arms and a closed end, each arm of said wires passing through one opening in said plug the closed ends of the U-shaped wires being directed toward the hip replacement and bent, along the plane formed by the arms of said U-shaped wire, away from the stem of said hip replacement to define an expansible and retractable guide to accommodate and center same, the open end of each of said U-shaped wire extending out of the openings in said plug being bent to contact and exert pressure on the medullary canal.

10. The apparatus of claim 9 wherein said adjusting means comprises a threaded screw having one end extending out of the prosthesis below the neck portion to contact the medullary canal.

11. The apparatus of claim 9 wherein said plug comprises four openings through which two U-shaped wires extend.

12. The apparatus of claim 9 wherein said plug has a diameter from about 0.3 to about 0.7 mm less than that of the medullary canal and is made of high density polyethylene.

13. A method of obtaining a centered hip replacement in a patient comprising (A) placing in the upper medullary canal of the paitent a trial hip prosthesis comprising a stem adapted to be fitted in the femur of a patient, a ball member, a neck portion connecting said stem and said ball member, and a laterally extending adjusting means disposed in said stem below the neck portion and having one end extending laterally out of the prosthesis below the neck portion to contact and not penetrate the medullary canal to selectively adjust the distance between the trial hip prosthesis and the upper medullary canal so as to center proximally said prosthesis with respect to the upper medullary canal of the femur of said patient, (B) centering said prosthesis with respect to said upper medullary canal with said adjusting means, (C) placing a pin across said femur and below the neck portion of said prosthesis to ascertain the centered position of said prosthesis, (D) removing said trial prosthesis, (E) placing in the medullary canal at a predetermined depth a device for distally centering said hip replacement and plugging the medullary canal, said device comprising a cylindrical plug for coaxial insertion into and blockage of the medullary canal, said plug being provided with a plurality of through bores or openings so oriented to be parallel to the longitudinal axis thereof, and means for accommodating and centering distally the distal end of said hip replacement said means comprising a plurality of U-shaped wires, each having an open end with two arms and a closed end, each wire passing through one opening in said plug, the closed ends of the U-shaped wires being directed toward the hip replacement and being bent along the plane formed by the arms of the U-shaped wire away from the stem of the replacement to define an expansible and retractable guide to accommodate and center the tip of said stem, the open end of said U-shaped wire extending out of the opening in said plug being bent to contact and exert pressure on the medullary canal, and (F) placing a hip replacement comprising a stem adapted to be fitted in the femur, a ball member, and a neck portion connecting said stem and said ball member, in said upper medullary canal, the stem of said hip replacement being received in the closed end of said U-shaped wires in said distally centering device and the lower part of the neck portion of said hip replacement being in contact with said pin placed across the femur.

14. The method of claim 13 including the additional steps of introducing a bone cement into the medullary canal between steps (E) and (F) and after step (F), removing the centering pin after the bone cement has cured.

15. The method of claim 13 wherein in step (E) said distally centering device is stored inside a hollow delivery tube and is placed in the medullary canal by inserting said delivery tube to a preselected depth in the medullary canal and pushing said distally centering device out of said delivery tube.

16. The method of claim 13 wherein step (E) is conducted first, followed by steps (A) through (D) and then step (F).

17. A method of centering distally the stem of a hip prosthesis comprising placing in the medullary canal at a predetermined depth a device for distally centering said hip prosthesis and plugging the medullary canal, said device comprising a cylindrical plug for coaxial insertion into and blockage of the medullary canal, said plug being provided with a plurality of through bores or openings so oriented to be parallel to the longitudinal axis of the plug, and means for accommodating and centering distally the stem of said hip replacement said means comprising a plurality of U-shaped wires each having an open end with two arms and a closed end, each arm passing through one opening in said plug, the closed end of the U-shaped wire being directed toward the hip prosthesis, the closed ends bent along the plane formed by the arms of the U-shaped wire away from the stem of the prosthesis to define an expansible and retractable guide to accommodate and center the tip of said stem, the open end of said U-shaped wire extending out of the opening in said plug being bent to contact and exert pressure on the medullary canal.

18. A method of centering proximally a hip prosthesis in the upper medullary canal of the femur of a patient comprising (A) placing in the upper medullary canal of the patient a trial hip prosthesis comprising a stem adapted to be fitted in the femur of a patient, a ball member, a neck portion connecting said stem and said ball member, and a laterally extending adjusting means disposed in said stem below the neck portion and having one end extending laterally out of the prosthesis below the neck portion to contact and not penetrate the medullary canal to selectively adjust the distance between the trial hip prosthesis and the upper medullary canal so as to center proximally said prosthesis with respect to the upper medullary canal of the femur of said patient, (B) centering said prosthesis with respect to said upper medullary canal with said adjusting means, (C) placing a pin across said femur and below the neck portion of said prosthesis to ascertain the centered position of said prosthesis, and (D) placing a hip replacement comprising a stem adapted to be fitted in the femur, a ball member, and a neck portion connecting said stem and said ball member, in said upper medullary canal.

* * * * *